US00PP12406P2

(12) United States Plant Patent
Utecht

(10) Patent No.: US PP12,406 P2
(45) Date of Patent: Feb. 12, 2002

(54) GERANIUM PLANT NAMED 'FISGOPI'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/773,005

(22) Filed: Jan. 31, 2001

(51) Int. Cl.[7] ..... A01H 5/00
(52) U.S. Cl. ..... Plt./325
(58) Field of Search ..... Plt./329, 325, 328

(56) References Cited

U.S. PATENT DOCUMENTS

PP9,230 P * 8/1995 Trees ..... Plt./325

OTHER PUBLICATIONS

2001 Fischer–Schmüllung Plant Alliance Catalogue featuring 'FISGOPI' on p. 17.
German Application and Denomination—'FISGOPI' (Dec. 15, 1998).
Official Gazette of the Community Plant Variety Rights Office—'FISGOPI' (Dec. 15, 1999), European Community Application and Grant (Jun. 11, 2000).
Canadian Application and Denomination, Plant Varieties Journal No. 38, Jan. 2001, Canada. pp. 55–56.
GTITM UPOVROM Citation for 'FISGOPI' as per QZ PBR 991470; Oct. 20, 1999.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisgopi', as described and illustrated, and particularly characterized by the combined features of pink semi-double flower with eyes, dark-green foliage with weak zonation, compact plant habit, and early spring flowering response.

1 Drawing Sheet

BACKGROUND OF THE INVENTION

The present invention comprises a new and distinct cultivar of geranium, botanically known as *Pelargonium zonale*, and hereinafter referred to by the cultivar name 'Fisgopi'.

'Fisgopi' is a product of a planned breeding program which had the objective of creating new geranium varieties with pink colored flowers with distinct markings, in combination with dark-green foliage. 'Fisgopi' originated from a hybridization made by the inventor Angelika Utecht in a controlled breeding program in Galdar, Gran Canaria, Spain, in 1996.

The female parent was the variety 'Roseball' (unpatented), Plant Breeder's Right in Europe, 'Penbab', having light pink semi-double flowers with distinct white eyes at the bases of upper petals, and medium green foliage with weak zonation. The male parent of 'Fisgopi' was a hybrid seedling, no. 1937-23 (unpatented), which was characterized by single-type, light-pink florets, dark-green foliage without zonation, and compact, round plant habit.

'Fisgopi' was selected as one flowering plant within the progeny of the stated cross by Angelika Utecht in 1997 in a controlled environment in Galdar, Gran Canaria, Spain. The first act of asexual reproduction of 'Fisgopi' was accomplished when vegetative cuttings were taken from the initial selection in the fall of 1997 in a controlled environment in Galdar, Gran Canaria, Spain, by, or under the supervision of, Angelika Utecht.

Horitultural examination of plants grown from cuttings of the plant initiated in May 1998 in Hillscheid, Federal Republic of Germany, and continuing thereafter, has demonstrated that the combination of characteristics as herein disclosed for 'Fisgopi' are firmly fixed and are retained through successive generations of asexual reproduction.

'Fisgopi' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basis characteristics of 'Fisgopi' in combination distinguish this geranium as a new and distinct cultivar:

1. Bright pink colored flowers with dark pink and white markings;
2. Numerous medium-sized inflorescences, well above the foliage;
3. Dark-green foliage with weak zonation;
4. Compact plant habit; and
5. Early spring flowering response.

Of the many commercial cultivars known to the present inventor, the most similar in comparison to 'Fisgopi' are the varieties 'Fisrosimo', U.S. plant patent application Ser. No. 09/323,108, and 'Fisbravo', U.S. plant Pat. No. 9,765.

In comparison to 'Fisrosimo', 'Fisgopi' has a slightly less bluish and more intense main flower color, rounder shaped umbels, borne higher above the foliage, leaves with weak zonation ('Fisrosimo' has no zonation), and earlier flowering time.

In comparison to 'Fisbravo', 'Fisgopi' has differently shaped flowers, rounder shaped umbels and longer peduncles. Furthermore, 'Fisgopi' has less intense reddish coloring of peduncles and pedicles.

BRIEF DESCRIPTION OF THE DRAWING

The accompanying photographic drawing shows typical flower and foliage characteristics of 'Fisgopi' with colors being as true as possible with an illustration of this type. The photograph is of a flowering potted plant. The measurements were taken in Langley, British Columbia, Canada, on Jul. 20, 2000, 15 weeks after planting of rooted cuttings into 6 inch pots. The plants had not been pinched.

In the following description color references are made to The Royal Horticultural Society Colour Chart. The color values were determined indoors from plants developed in a greenhouse in May 2000, in Hillscheid, Germany.

Classification:

*Botanical.*—A hybrid of the species *Pelargonium zonale* L'Hérit.

*Commercial.*—Zonal geranium, cv. 'Fisgopi'.

Inflorescence:

*Umbel.*—Shape: Nearly semi-spherical. Average diameter: 118 mm. Umbel depth: 65 mm. Peduncle length: 194 mm. Peduncle color: Mainly green, RHS 137 D, reddish RHS 179 infused in parts. Pedicel length: 30 mm. Pedicel color: Ranges from RHS 179 B to 179 A. Number of flowers per umbel: About 30–40. Lastingness of umbel: Approximately 18 days.

*Corolla.*—Average diameter: 45 mm. Form: Weakly Semi-double. Shape: Round outline, with a gap between the upper and lower petals. Number of petaloids: 1–3. Color of petaloids: Upper surface RHS 68 B, lower surface RHS 65 A or lighter. Number of petals: 5–6. Size of petals: Upper petals 25–26 mm long, 18–20 mm wide; lower petals 24–25 mm long, 22–24 mm wide. Shape of petals: Oblong to nearly obovate, upper end rounded, attenuate base, margin usually entire. Color (general tonality from a distance of three meters): Bright pink with dark pink eyes and white center. Color of upper petals: Main color RHS 68 A. Markings of upper petals: Dark pink eyes, RHS 67 C, and with white bases, RHS 155 D, and reddish veins, RHS 57 C. Color of lower petals: Main color RHS 67 D. Markings of lower petals: Small rose eyes, RHS 52 A, and with small bases varying from white RHS 155 D to very light pink, RHS 179 B. Color of lower surface of petals: Mainly very light pink, variable between RHS 65 A and RHS 65 D. Color of sepals: Outer surface green, RHS 143 C, red base RHS 179 A; inner surface green, RHS 143 C, light reddish-brown base, approximately RHS 179 B. Number of sepals: 5.

*Bud*: (*just prior to petals unfolding*).—Shape: Elliptical. Color (lower part — sepals): Green, RHS 137 D, with a weak reddish spot at the base, RHS 181 A or lighter. Color (upper part — petals): Pink, RHS 54 B. Length: 15 mm. Width: 8 mm. Size of sepals: 11–13 mm long, 4–5 mm wide for the largest, upper sepal, 3 mm wide for other sepals. Shape of sepals: Linear to lanceolate, acute tip, base truncate, surface weak with pubescence, margin entire.

*Reproductive organs.*—Androecium: 3–5 fertile anthers, white filaments, yellow-orange pollen RHS 30 A, moderate quantity of pollen produced. Gynoecium: 5–6-lobed stigma, whitish filament, one pistil per flower. Fertility/Seed set: Occasionally a few seeds are developed, oblong shape, 4–5 mm long, brown, RHS 177B. Fruit: Oblong shape, approximately 6 mm long, rostrum approximately 40 mm long when ripe, color RHS 143 C.

*Spring flowering response period.*—In Hillscheid, Germany, in 2000, plant had on average 1.8 flowers opened 9 weeks after planting of rooted cuttings.

*Outdoor flower production.*—Relatively rich flowering the flower count in 2000 in Hillscheid, Germany, indicated about 4–5 inflorescences per plant in mid-May.

*Durability.*—Good stability of flower color, relatively good rain resistance.

*Lastingness of individual bloom.*—Approximately 8–9 days at 18° C.

*Fragrance.*—None.

Plant:

*Foliage.*—Form: Kidney-shaped, with open to wide open base, somewhat wavy margin, weak expression of lobes. Apex: Rounded. Base: Open to wide open, cordate. Margin: Bicrenated. Texture: Upper surface is dull, slightly velvety due to weak pubescence. Size of leaf: 79 mm wide, 48–52 mm long. Color of upper surface: Dark-green, approximately RHS 137 A. Color of lower surface: RHS 137 D. Color of zonation: Weak, brown, approximately RHS 166 A. Petiole size: 45–55 mm in length, 3 mm in diameter. Petiole color: Light green, RHS 143 C.

*General appearance and form.*—Stem color: Green, RHS 137 C. Internode length: 10 mm. Branching pattern: 4.9 branches. Plant size: 25.5 cm in width to 28.5 cm in height, measured from the soil to the surface of the foliage (without the inflorescence).

Disease/pest resistance/susceptibility: None observed to date.

I claim:

1. A new and distinct cultivar of geranium plant named 'Fisgopi', as described and illustrated.

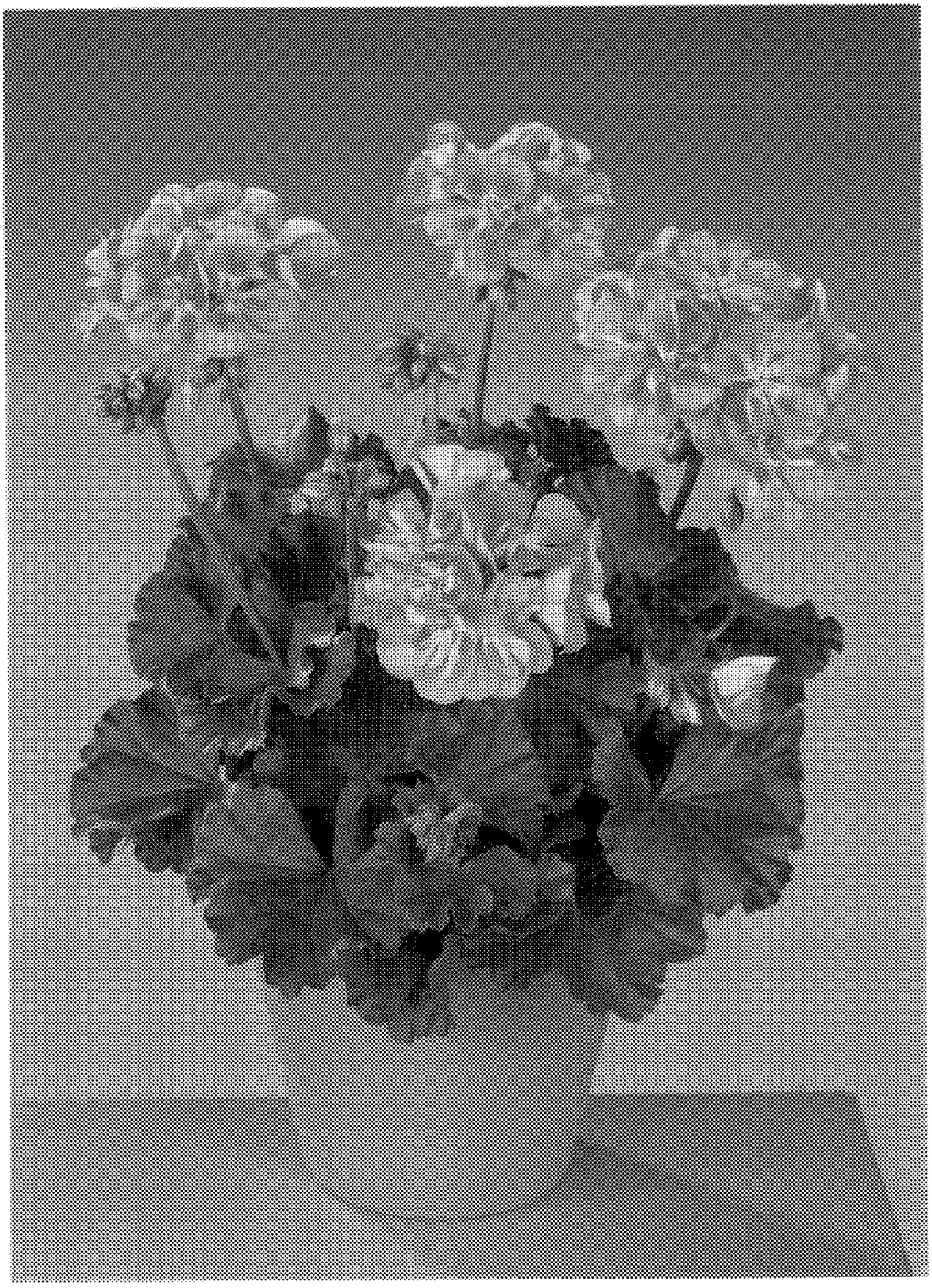

* * * * *